US012070337B2

(12) United States Patent
Jin

(10) Patent No.: US 12,070,337 B2
(45) Date of Patent: Aug. 27, 2024

(54) SYSTEM FOR DIAGNOSING MENTAL DISORDERS USING NEUROMETRICS

(71) Applicant: WAVE NEUROSCIENCE, INC., Newport Beach, CA (US)

(72) Inventor: Yi Jin, Irvine, CA (US)

(73) Assignee: WAVE NEUROSCIENCE, INC., Newport Beach, CA (US)

( * ) Notice: Subject to any disclaimer, the term of this patent is extended or adjusted under 35 U.S.C. 154(b) by 1146 days.

(21) Appl. No.: 16/870,958

(22) Filed: May 9, 2020

(65) Prior Publication Data

US 2020/0345310 A1 Nov. 5, 2020

Related U.S. Application Data

(60) Division of application No. 15/154,523, filed on May 13, 2016, now Pat. No. 10,682,096, which is a continuation-in-part of application No. 15/087,209, filed on Mar. 31, 2016, now Pat. No. 10,420,482.

(51) Int. Cl.
*A61B 5/00* (2006.01)
*A61B 5/16* (2006.01)
*A61B 5/374* (2021.01)

(52) U.S. Cl.
CPC ............ *A61B 5/7257* (2013.01); *A61B 5/165* (2013.01); *A61B 5/374* (2021.01); *A61B 5/4088* (2013.01)

(58) Field of Classification Search
CPC ....... A61B 5/7257; A61B 5/165; A61B 5/374; A61B 5/4088
See application file for complete search history.

(56) References Cited

U.S. PATENT DOCUMENTS

| | | | |
|---|---|---|---|
| 2008/0167571 A1 | 7/2008 | Gevins | |
| 2015/0099946 A1* | 4/2015 | Sahin | A61B 7/04 600/301 |
| 2015/0351655 A1* | 12/2015 | Coleman | G16H 50/20 600/595 |
| 2018/0184964 A1* | 7/2018 | Simon | A61B 5/162 |
| 2019/0209097 A1* | 7/2019 | Martien | A61B 5/7282 |

OTHER PUBLICATIONS

Mathewson et al., "Regional EEG alpha power, coherence, and behavioral symptomatology in autism spectrum disorder", Clinical Neurophysiology, 123(9), pp. 1798-1809 (Year: 2012).*
Lefebvre et al., "Alpha Waves as a Neuromarker of Autism Spectrum Disorder: The Challenge of Reproducibility and Heterogeneity", Front. Neurosci., Sec. Brain Imaging Methods vol. 12 (Year: 2018).*
Simon et al. ("Dysfunction of sensory oscillations in Autism Spectrum Disorder", Neuroscience & Biobehavioral Reviews, vol. 68, pp. 848-861 (Year: 2016).*

(Continued)

*Primary Examiner* — Jacqueline Cheng
*Assistant Examiner* — Tho Q Tran
(74) *Attorney, Agent, or Firm* — Buchalter, a Professional Corporation

(57) ABSTRACT

Described are novel systems for the diagnosis of specific mental disorders using neurometrics. EEG parameters are compared to thresholds to determine if a person is suffering from autism spectrum disorder, Alzheimer's disease, anxiety, depression, or schizophrenia.

9 Claims, 11 Drawing Sheets

(56) References Cited

OTHER PUBLICATIONS

Adler G., et al., "EEG Coherence in Alzheimer's Dementia," Journal of Neural Transmission, 2003, vol. 110, pp. 1051-1058.
Bonanni L., et al., "EEG Comparisons in Early Alzheimer's Disease, Dementia with Lewy Bodies and Parkinson's Disease with Dementia Patients with a 2-Year Follow-up," Brain, 2008, vol. 131, pp. 690-705.
Dunkin J.J., et al., "Relationships Between EEG Coherence and Neurophychological Tests in Dementia," Clinical Electroencephalography, 1995, vol. 26 (1), pp. 47-59.
Locatelli T., et al., "EEG Coherence in Alzheimer's Disease," Electroencephalography and clinical Neurophysiology, 1998, vol. 106, pp. 229-237.
Moretti D.V., et al., "Individual Analysis of EEG Frequency and Band Power in Mild Alzheimer's Disease," Clinical Neurophysiology, Feb. 2004, vol. 115 (2), pp. 299-308.
Prinz P.N., et al., "Dominant Occipital (alpha) Rhythm Frequency in Early Stage Alzheimer's Disease and Depression," Electroencephalography & Clinical Neurophysiology, Nov. 1989, vol. 73 (5), Abstract only.
Sankari Z., et al., "Intrahemispheric, Interhemispheric, and Distal EEG Coherence in Alzheimer's Disease," Clinical Neurophysiology, 2011, vol. 122, pp. 897-906.
Verner K., et al., "Electroencephalographic Coherence in Alzheimer's Disease: Comparisons with a Control Group and Population Norms," Journal of Geriatric Psychiatry and Neurology, 2000, vol. 13, pp. 1-8.

\* cited by examiner

SYSTEM FOR DIAGNOSING MENTAL DISORDERS USING NEUROMETRICS

CROSS-REFERENCE TO RELATED APPLICATIONS

This application is a divisional of U.S. patent application Ser. No. 15/154,523, filed May 13, 2016, now U.S. Pat. No. 10,682,096, which is a continuation-in-part of U.S. patent application Ser. No. 15/087,209, filed Mar. 31, 2016, now U.S. Pat. No. 10,420,482, each of which is incorporated herein by reference in its entirety.

BACKGROUND OF THE INVENTION

Mental disorders can be painful, debilitating, and very costly for the affected individual and their family. Approximately one in five adults in the US experiences a mental disorder in a given year. 18.1% of adults in the US experience an anxiety disorder, such as posttraumatic stress disorder, obsessive-compulsive disorder and specific phobias. 6.9% of adults in the US have at least one major depressive episode each year. 1.1% of adults in the US live with schizophrenia.

The consequences of lack of treatment are significant. Mental disorders are the third most common cause of hospitalization in the US for both youth and adults aged 18-44. Suicide is the $10^{th}$ leading cause of death in the US, and the $2^{nd}$ leading cause of death for those aged 15-24. Each day, approximately 18-22 veterans die by suicide.

A key factor in treatment of mental disorders is proper diagnosis. The standard method of diagnosing mental disorders has been with either the Diagnostic and Statistical Manual of Mental Disorders (DSM) or the International Statistical Classification of Diseases and Related Health Problems (ICD), Chapter 5: Mental and behavioural disorders. Both standards primarily involve diagnosis using conversation with the patient regarding symptoms and behavior. This has the disadvantage of being subjective, based on the interviewer, which lessens the diagnostic reliability, sometimes resulting in two clinicians coming to different diagnoses of the same patient.

DSM and ICD are primarily concerned with the signs and symptoms of mental disorders, rather than the underlying causes. This reflects a general lack of pathophysiological understanding of mental disorders.

It is apparent that a repeatable and reliable system for the diagnosis of mental disorders that is based on measurable data, independent of the interpretation of an interviewer, would provide significant benefit to patients and to the psychiatric community.

SUMMARY

Certain terms are used that are necessary for a better understanding of the systems described herein. The definitions of these terms are given in the detailed description.

Described herein are novel systems to provide a diagnosis of mental disorders for a person using characteristics of the person's EEG. The systems described herein do not require any measurement other than the EEG, although the systems do not preclude the use of other measurements in order to confirm or validate the diagnosis. The systems described herein make use of the measurement locations described in the internationally recognized 10-20 system, although other, possibly higher resolution, systems could also be used.

In one aspect is a system for diagnosing autism spectrum disorder (ASD) that comprises: (a) an EEG recording device for recording the EEG of a person; and (b) a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and (c) a diagnosis mechanism where the system diagnoses the person with ASD if the average relative frontal Alpha Power is less than about ten percent of the average relative occipital-parietal Alpha Power. The diagnosis mechanism can be a processor or a hand calculation.

In another aspect is a system for diagnosing ASD that comprises: (a) an EEG recording device for recording the EEG of a person; (b) a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and (c) a diagnosis mechanism where the system diagnoses the person with ASD if the average relative frontal Alpha Power is less than about twenty percent of the average relative occipital-parietal Alpha Power and the average relative frontal Alpha Power is less than about 5%. The diagnosis mechanism can be a processor or a hand calculation.

In another aspect is a system for diagnosing ASD that comprises: (a) an EEG recording device for recording the EEG of a person; (b) a processing device comprising a processor and internal or external memory, in order to calculate the average Alpha Frequency of EEG signals from at least one of the frontal EEG channels and the average Alpha Frequency of EEG signals from at least one of the occipital-parietal EEG channels; and (c) a diagnosis mechanism where the system diagnoses the person with ASD if the average frontal Alpha Frequency is greater than about 0.5 Hz more than the average occipital-parietal Alpha Frequency. The diagnosis mechanism can be a processor or a hand calculation.

The aspects described may be used individually or as a combination. By requiring more than one metric to be satisfied for a diagnosis, the confidence of the diagnosis may improve.

In some embodiments of at least one aspect described above, the system diagnoses the person with ASD if the average relative frontal Alpha Power is less than about ten percent of the average relative occipital-parietal Alpha Power and the average relative frontal Alpha Power is less than about 5%.

In some embodiments of at least one aspect described above, the system diagnoses the person with ASD if the average relative frontal Alpha Power is less than about ten percent of the average relative occipital-parietal Alpha Power and the average frontal Alpha Frequency is greater than about 0.5 Hz more than the average occipital-parietal Alpha Frequency.

In some embodiments of at least one aspect described above, the system diagnoses the person with ASD if the average relative frontal Alpha Power is less than about twenty percent of the average relative occipital-parietal Alpha Power and the average relative frontal Alpha Power is less than about 5% and the average frontal Alpha Frequency is greater than about 0.5 Hz more than the average occipital-parietal Alpha Frequency.

In one aspect is a system for diagnosing Alzheimer's disease that comprises: (a) an EEG recording device for recording the EEG of a person; (b) a processing device comprising a processor and internal or external memory, in order to calculate the average dominant frequency between about 5 Hz and 15 Hz of EEG signals from at least one EEG channel; and (c) a diagnosis mechanism where the system diagnoses the person with Alzheimer's Disease if the average dominant frequency is less than about 8 Hz. The diagnosis mechanism can be a processor or a hand calculation.

In another aspect is a system for diagnosing Alzheimer's disease that comprises: (a) an EEG recording device for recording the EEG of a person; (b) a processing device comprising a processor and internal or external memory, in order to calculate the average dominant frequency between about 5 Hz and 15 Hz of EEG signals from at least one EEG channel and the average coherence at the dominant frequency between the EEG signals from at least one frontal EEG channel and at least one occipital-parietal EEG channel; and (c) a diagnosis mechanism where the system diagnoses the person with Alzheimer's Disease if the average coherence is less than about 10%. The diagnosis mechanism can be a processor or a hand calculation.

In some embodiments of at least one aspect described above, the system diagnoses the person with Alzheimer's disease if the dominant frequency is less than about 8 Hz and the average coherence is less than about 10%.

In one aspect is a system for diagnosing Anxiety Disorder that comprises: (a) an EEG recording device for recording the EEG of a person; (b) a processing device comprising a processor and internal or external memory, in order to calculate the average entropy of the EEG signals from at least one EEG channel; and (c) a diagnosis mechanism where the system diagnoses the person with Anxiety Disorder if the average entropy is greater than about 0.7. The diagnosis mechanism can be a processor or a hand calculation.

In one aspect is a system for diagnosing Depression that comprises: (a) an EEG recording device for recording the EEG of a person; (b) a processing device comprising a processor and internal or external memory, in order to calculate the average relative Alpha Power of at least one frontal EEG channel and the average relative Alpha Power of at least one occipital-parietal EEG channel; and (c) a diagnosis mechanism where the system diagnoses the person with Depression if the average relative frontal Alpha Power is greater than the average relative occipital-parietal Alpha Power. The diagnosis mechanism can be a processor or a hand calculation.

In another aspect is a system for diagnosing Depression that comprises: (a) an EEG recording device for recording the EEG of a person; (b) a processing device comprising a processor and internal or external memory, in order to calculate the average frontal Alpha Frequency of EEG signals from at least one frontal EEG channel; and (c) a diagnosis mechanism where the system diagnoses the person with Depression if the average relative Q-factor about the average frontal Alpha Frequency of EEG signals from at least one frontal EEG channel is greater than about 8. The diagnosis mechanism can be a processor or a hand calculation.

In some embodiments of at least one aspect described above, the system diagnoses the person with Depression if the average relative frontal Alpha Power is greater than the average relative occipital-parietal Alpha Power and the average relative Q factor is greater than about 8.

In one aspect is a system for diagnosing Schizophrenia that comprises: (a) an EEG recording device for recording the EEG of a person; (b) a processing device comprising a processor and internal or external memory, in order to calculate the average dominant frequency $f_d$ between about 5 Hz and 15 Hz of EEG signals from at least one EEG channel, the average lower dominant frequency between about 5 Hz and about $f_d$-1 Hz of EEG signals from at least one EEG channel, and the average upper dominant frequency between about $f_d$+1 Hz and about 15 Hz of EEG signals from at least one EEG channel; and (c) a diagnosis mechanism where the system diagnoses the person with Schizophrenia if the magnitude of the average power spectrum from at least one EEG channel at the lower dominant frequency is at least about 80% of the magnitude of the average power spectrum from at least one EEG channel at the dominant frequency or the magnitude of the average power spectrum from at least one EEG channel at the upper dominant frequency is at least about 80% of the magnitude of the average power spectrum from at least one EEG channel at the dominant frequency. The diagnosis mechanism can be a processor or a hand calculation.

BRIEF DESCRIPTION OF THE DRAWINGS

A better understanding of the features and advantages of the systems provided will be obtained by reference to the following detailed description that sets forth illustrative embodiments and the accompanying drawings of which.

DETAILED DESCRIPTION

Figure 1:
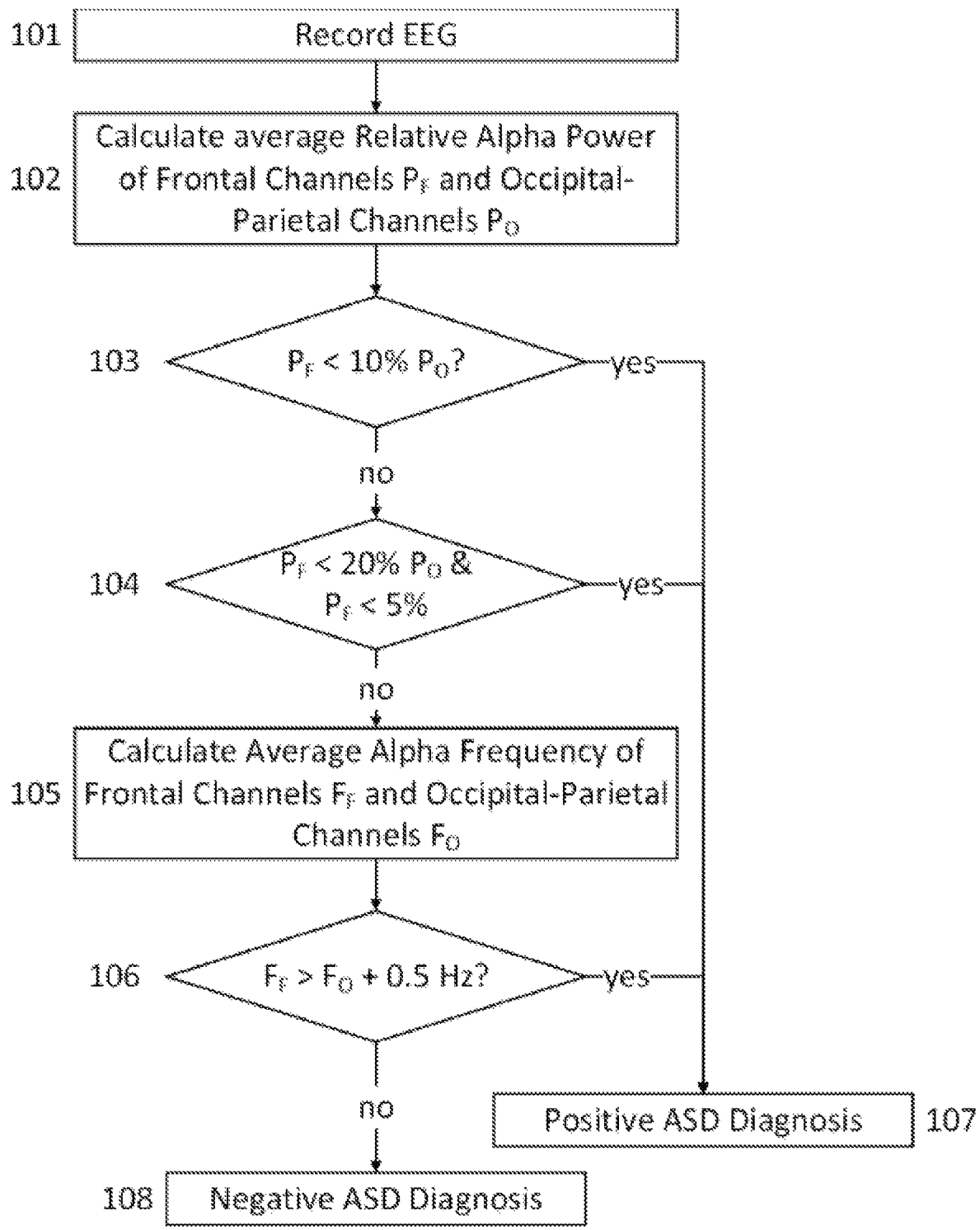
FIG. 1 shows an exemplary system in which a diagnosis of autism is determined based upon the relative Alpha Power of the frontal EEG channels and the occipital-parietal EEG channels, or based upon the difference between the frontal alpha frequency and the occipital-parietal alpha frequency.

While certain embodiments have been provided and described herein, it will be readily apparent to those skilled in the art that such embodiments are provided by way of example only. It should be understood that various alternatives to the embodiments described herein may be employed, and are part of the invention described herein.

Described herein are systems for diagnosing mental disorders using characteristics of the EEG of a person. The systems described herein include diagnosis of autism spectrum disorder (ASD), Alzheimer's disease, anxiety, depression, and schizophrenia. The mental disorders described herein also encompass all subtypes derived from the mental disorder. For example, diagnosis of anxiety also comprises diagnosis of bulimia, anorexia nervosa, obsessive-compulsive disorder, post-traumatic stress disorder, generalized anxiety disorder, and panic disorder. Diagnosis of ASD also comprises diagnosis of Asperger's syndrome and childhood disintegrative disorder. Diagnosis of depression also comprises diagnosis of dysthymia, bipolar depression, seasonal depressive disorder, and depressive episode. Diagnosis of schizophrenia also comprises diagnosis of paranoid schizophrenia, disorganized schizophrenia, and catatonic schizophrenia. Diagnosis of Alzheimer's disease also comprises diagnosis of inflammatory, non-inflammatory, and cortical Alzheimer's disease, as well as dementia and mild cognitive impairment.

The term "diagnosis," when referring to the systems described herein, is the identification of the nature of a mental disorder by EEG analysis where the confidence that the diagnosis is correct is at least 90%.

The term "Fast Fourier Transform," or FFT, when referring to the systems described herein, is the calculation algorithm to determine the frequency spectrum of a signal from an EEG channel.

The term "Alpha Power," when referring to the systems described herein, is the sum of the magnitude squared of the FFT values in the alpha range (about 8 Hz to about 13 Hz).

The term "total power," when referring to the systems described herein, is the sum of the magnitude squared of the FFT values across the frequency spectrum from about 0 Hz to about half the sampling frequency.

The term "relative Alpha Power," when referring to the systems described herein, is the Alpha Power divided by the total power.

The term "average relative Alpha Power," when referring to the systems described herein, is the average value of the relative Alpha Power for at least one of the EEG channels.

The term "dominant frequency," when referring to the systems described herein, is the frequency associated with the highest spectral density within a specified range.

The term "alpha frequency," when referring to the systems described herein, is the dominant frequency within the alpha range.

The term "10-20 system," when referring to the systems described herein, is the internationally recognized method to describe the location of scalp electrodes in the context of an EEG recording. The locations are divided into frontal, central, temporal, parietal, and occipital regions. Each location has a label, based on the region where it is located.

The term "frontal channels," when referring to the systems described herein, is the set of EEG channels in locations above the frontal and pre-frontal region of the brain. For example, in the 10-20 system, the frontal channels comprise Fp1, Fp2, Fz, F3, F4, F7, and F8.

The term "occipital-parietal channels," when referring to the systems described herein, is the set of EEG channels in locations above the occipital and parietal regions of the brain. For example, in the 10-20 system, the occipital-parietal channels comprise Pz, P3, P4, O1, and O2.

The term "coherence," when referring to the systems described herein, is used to quantify common frequencies and evaluate the similarity of two signals. It is determined by dividing the magnitude-squared cross-spectral density between the two signals by the product of the spectral density of each signal at the frequency of interest.

The term "spectral density," when referring to the systems described herein, is a measure of the power of an EEG signal at a specified frequency, and is the Fourier transform of the auto-correlation function of the signal.

The term, "cross-spectral density," when referring to the systems described herein, is the Fourier transform of the cross-correlation of two EEG signals.

The term, "total spectral power," when referring to the systems described herein, is the total energy of an EEG signal, and is the sum of the spectral density over all frequencies.

The term "entropy," when referring to the systems described herein, is a measure of the system complexity. A high entropy EEG signal is a result of a large number of processes occurring in the brain. Entropy is determined for an EEG signal in two stages. First a normalized power spectrum is generated by dividing the spectral density by the total spectral power, as shown in the equation below:

$$S_n(f) = \frac{S(f)}{\Sigma_f S(f)}$$

where $S_n$ is the normalized power spectrum and $S$ is the spectral density. Then, the entropy is calculated as the sum across the frequency spectrum from 0 Hz to half the sampling frequency of the normalized spectrum multiplied by the log base two of the inverse power spectrum, as shown in the equation below:

$$E = \Sigma_f S_n(f) \log_2 \frac{1}{S_n(f)}$$

where E is the entropy.

The term "Q-factor," when referring to the systems described herein, is a measure of the frequency selectivity of the EEG signal about a specified frequency. A high Q-factor signal has a spectral distribution that is concentrated around the specified frequency, whereas a low Q-factor signal has a spectral distribution that is more widely spread about the specified frequency. Q-factor is calculated as the specified frequency divided by the half-power bandwidth. The half-power bandwidth is the width of the power spectrum at half the power spectrum value at the specified frequency.

As used herein, reference to "a hand calculation" refers to one that does not require a processor. Thus, the hand calculation can be done by, for example, a person making mathematical calculations and/or determining if one number is larger or smaller than another number and/or whether a number falls within a certain range.

Described herein are systems for diagnosing one or more mental disorders in a person using characteristics of the EEG of a person, which may include, but do not necessarily require, additional information, such as information regarding the person's symptoms, demographic data, genome analysis, vital signs, treatment history, or current medication.

The brain may be thought of as a physical system, where the goal, in addition to providing thought processes and autonomic function, includes minimization of energy consumption. The brain processes are brought about through electrochemical signaling between neurons. This electrochemical signaling is not random, but instead often occurs at or near a specified frequency. Therefore, the brain may also be thought of as a pseudo-resonant system, with the resonant frequency equal to its alpha frequency, or dominant EEG frequency between about 8 Hz to about 13 Hz.

A resonant system is lower energy than a non-resonant system, and it is this resonance that contributes to the minimization of energy consumption by the brain. Therefore, in the brain a tradeoff exists between complex neuronal behavior provided for rational thought and other processes the brain must serve, and minimization of energy consumed by the brain. When the characteristics of resonant activity of the brain are altered from their "normal" values, symptoms of mental orders may occur, based in part on the particular change in the EEG characteristics.

If the relative Alpha Power of the frontal region of the brain is significantly reduced compared to the Alpha Power in the occipital-parietal region, symptoms of ASD may occur, and a diagnosis of ASD is appropriate. Often, the alpha frequency measured in the occipital-parietal region of the brain is different than the alpha frequency in the frontal region of the brain. It is not uncommon for the occipital-parietal alpha frequency to be up to 1 Hz higher than the frontal alpha frequency. However, if the frontal alpha frequency is more than 0.5 Hz higher than the occipital-parietal alpha frequency, then symptoms of ASD may also occur, and a diagnosis of ASD is appropriate. If both EEG characteristics occur together, the confidence in the diagnosis may increase.

In one aspect the invention provides systems for diagnosing autism spectrum disorder (ASD) that comprise: (a) an EEG recording device for recording the EEG of a person; (b) a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and (c) a diagnosis mechanism where the system diagnoses the person with ASD if the average relative frontal Alpha Power is less than about ten percent of the average relative occipital-parietal Alpha Power. The diagnosis mechanism can be a processor or hand calculation.

In another aspect is a system for diagnosing ASD that comprises: (a) an EEG recording device for recording the EEG of a person; (b) a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and (c) a diagnosis mechanism where the system diagnoses the person with ASD if the average relative frontal Alpha Power is less than about twenty percent of the average relative occipital-parietal Alpha Power and the average relative frontal Alpha Power is less than about 5%. The diagnosis mechanism can be a processor or a hand calculation.

In another aspect is a system for diagnosing ASD that comprises: (a) an EEG recording device for recording the EEG of a person; (b) a processing device comprising a processor and internal or external memory, in order to calculate the average alpha frequency of EEG signals from at least one of the frontal EEG channels and the average alpha frequency of EEG signals from at least one of the occipital-parietal EEG channels; and (c) a diagnosis mechanism where the system diagnoses the person with ASD if the average frontal alpha frequency is greater than about 0.5 Hz more than the average occipital-parietal alpha frequency. The diagnosis mechanism can be a processor or a hand calculation.

The aspects described may be used individually or as a combination. By requiring more than one metric to be satisfied for a diagnosis, the sensitivity of the diagnosis may improve.

In some embodiments of at least one aspect described above, the system diagnoses the person with ASD if the average relative frontal Alpha Power is less than about 10% of the average relative occipital-parietal Alpha Power and the average relative frontal Alpha Power is less than about 5%.

In some embodiments of at least one aspect described above, the system diagnoses the person with ASD if the average relative frontal Alpha Power is less than about 10% of the average relative occipital-parietal Alpha Power and the average frontal alpha frequency is greater than about 0.5 Hz more than the average occipital-parietal alpha frequency.

In some embodiments of at least one aspect described above, the system diagnoses the person with ASD if the average relative frontal Alpha Power is less than about 20% of the average relative occipital-parietal Alpha Power and the average relative frontal Alpha Power is less than about 5% and the average frontal Alpha Frequency is greater than about 0.5 Hz more than the average occipital-parietal Alpha Frequency.

The dominant frequency in the range between about 5 Hz to about 15 Hz, in normal individuals who are awake, relaxed, with eyes closed, is equal to the alpha frequency. The alpha frequency has a normal range between 8 Hz-13 Hz, but if the alpha frequency drops below 8 Hz, then symptoms of dementia, mild cognitive impairment, or Alzheimer's may occur. In addition, these symptoms may occur if the coherence of brain EEG activity between the frontal and occipital-parietal regions of the brain drops to a low value, resulting in reduced communication between the regions of the brain and reduced cognitive performance. In either case, a diagnosis of Alzheimer's disease is appropriate.

In one aspect the subject invention provides a system for diagnosing Alzheimer's disease that comprises: (a) an EEG recording device for recording the EEG of a person; (b) a processing device comprising a processor and internal or external memory, in order to calculate the average dominant frequency between about 5 Hz and 15 Hz of EEG signals from at least one EEG channel; and (c) a diagnosis mechanism where the system diagnoses the person with Alzheimer's Disease if the average dominant frequency is less than about 8 Hz. The diagnosis mechanism can be a processor or a hand calculation.

In another aspect is a system for diagnosing Alzheimer's disease that comprises: (a) an EEG recording device for recording the EEG of a person; (b) a processing device comprising a processor and internal or external memory, in order to calculate the average dominant frequency between about 5 Hz and 15 Hz of EEG signals from at least one EEG channel and the average coherence at the dominant frequency between the EEG signals from at least one frontal EEG channel and at least one occipital-parietal EEG channel; and (c) a diagnosis mechanism where the system diagnoses the person with Alzheimer's Disease if the average coherence is less than about 10%. The diagnosis mechanism can be a processor or a hand calculation.

In some embodiments of at least one aspect described above, the system diagnoses the person with Alzheimer's disease if the dominant frequency is less than about 8 Hz and the average coherence is less than about 10%.

The EEG of someone awake, relaxed, with eyes closed is normally rhythmic, with most of the energy in the signal centered around that alpha frequency. If the brain activity is more chaotic and contains energy that is distributed widely across multiple frequency bands, the person may have symptoms of anxiety, and an anxiety diagnosis is appropriate. The frequency distribution can be measured by determining the entropy of the power spectrum across all EEG channels. If the entropy is high, then an autism diagnosis is appropriate.

In one aspect is a system for diagnosing Anxiety Disorder that comprises: (a) an EEG recording device for recording the EEG of a person; (b) a processing device comprising a processor and internal or external memory, in order to calculate the average entropy of the EEG signals from at least one EEG channel; and (c) a diagnosis mechanism where the system diagnoses the person with Anxiety Disorder if the average entropy is greater than about 0.7. The diagnosis mechanism can be a processor or a hand calculation.

In a normal person, the Alpha Power is concentrated around the posterior portion of the brain, with less Alpha Power present in the frontal region. If the concentration of Alpha Power is farther anterior in the brain, then the person may experience symptoms of depression, requiring a depression diagnosis. In addition, the brain of a depressed person will often be highly rhythmic, and therefore have lower energy. A highly rhythmic brain can be shown by calculating the Q-factor of the EEG signal. A high Q-factor in the frontal region of the brain may result in symptoms of depression, and a depression diagnosis is appropriate.

In one aspect is a system for diagnosing Depression that comprises: (a) an EEG recording device for recording the EEG of a person; (b) a processing device comprising a processor and internal or external memory, in order to calculate the average relative Alpha Power of at least one frontal EEG channel and the average relative Alpha Power of at least one occipital-parietal EEG channel; and (c) a diagnosis mechanism where the system diagnoses the person with Depression if the average relative frontal Alpha Power is greater than the average relative occipital-parietal Alpha Power. The diagnosis mechanism can be a processor or a hand calculation.

In another aspect is a system for diagnosing Depression that comprises: (a) an EEG recording device for recording the EEG of a person; (b) a processing device comprising a processor and internal or external memory, in order to calculate the average frontal Alpha Frequency of EEG signals from at least one frontal EEG channel; and (c) a diagnosis mechanism where the system diagnoses the person with Depression if the average relative Q-factor about the average frontal Alpha Frequency of EEG signals from at least one frontal EEG channel is greater than about 8. The diagnosis mechanism can be a processor or a hand calculation.

In some embodiments of at least one aspect described above, the system diagnoses the person with Depression if the average relative frontal Alpha Power is greater than the average relative occipital-parietal Alpha Power and the average relative Q factor is greater than about 8.

Normally, the power spectrum of the EEG of a person contains a single dominant frequency when relaxed, awake, with eyes closed, which is the alpha frequency. This frequency can be different between the occipital-parietal and frontal portions of the brain. However, if the EEG of the person contains multiple dominant frequencies at least about 1 Hz apart, each being of similar power, then the person may experience symptoms of schizophrenia, and is given a schizophrenia diagnosis.

In one aspect is a system for diagnosing Schizophrenia that comprises: (a) an EEG recording device for recording the EEG of a person; (b) a processing device comprising a processor and internal or external memory, in order to calculate the average dominant frequency ($f_d$) between about 5 Hz and 15 Hz of EEG signals from at least one EEG channel, the average lower dominant frequency between about 5 Hz and about $f_d$−1 Hz of EEG signals from at least one EEG channel, and the average upper dominant frequency between about $f_d$+1 Hz and about 15 Hz of EEG signals from at least one EEG channel; and (c) a diagnosis mechanism where the system diagnoses the person with Schizophrenia if the magnitude of the average power spectrum from at least one EEG channel at the lower dominant frequency is at least about 80% the magnitude of the average power spectrum from at least one EEG channel at the dominant frequency or the magnitude of the average power spectrum from at least one EEG channel at the upper dominant frequency is at least about 80% the magnitude of the average power spectrum from at least one EEG channel at the dominant frequency. The diagnosis mechanism can be a processor or a hand calculation.

FIG. 1 shows an exemplary flow diagram of a system to diagnose ASD. In this example, the EEG of the person is recorded (101) and the average relative Alpha Power of the frontal channels and occipital-parietal channels is found (102). If the frontal power is less than 10% the occipital-parietal power (103), then an ASD diagnosis is made (107). Otherwise, the criteria is changed such that if the frontal power is less than 20% the occipital-parietal power and the frontal power is less than 5% (104), then an ASD diagnosis is made. If both of these criteria are not met, the average alpha frequency for the frontal EEG channels and the occipital-parietal channels is calculated (105), and an ASD diagnosis is made if the frontal alpha frequency is at least 0.5 Hz greater than the occipital-parietal alpha frequency. If no criteria are met, then an ASD diagnosis is not appropriate (108).

Figure 2:
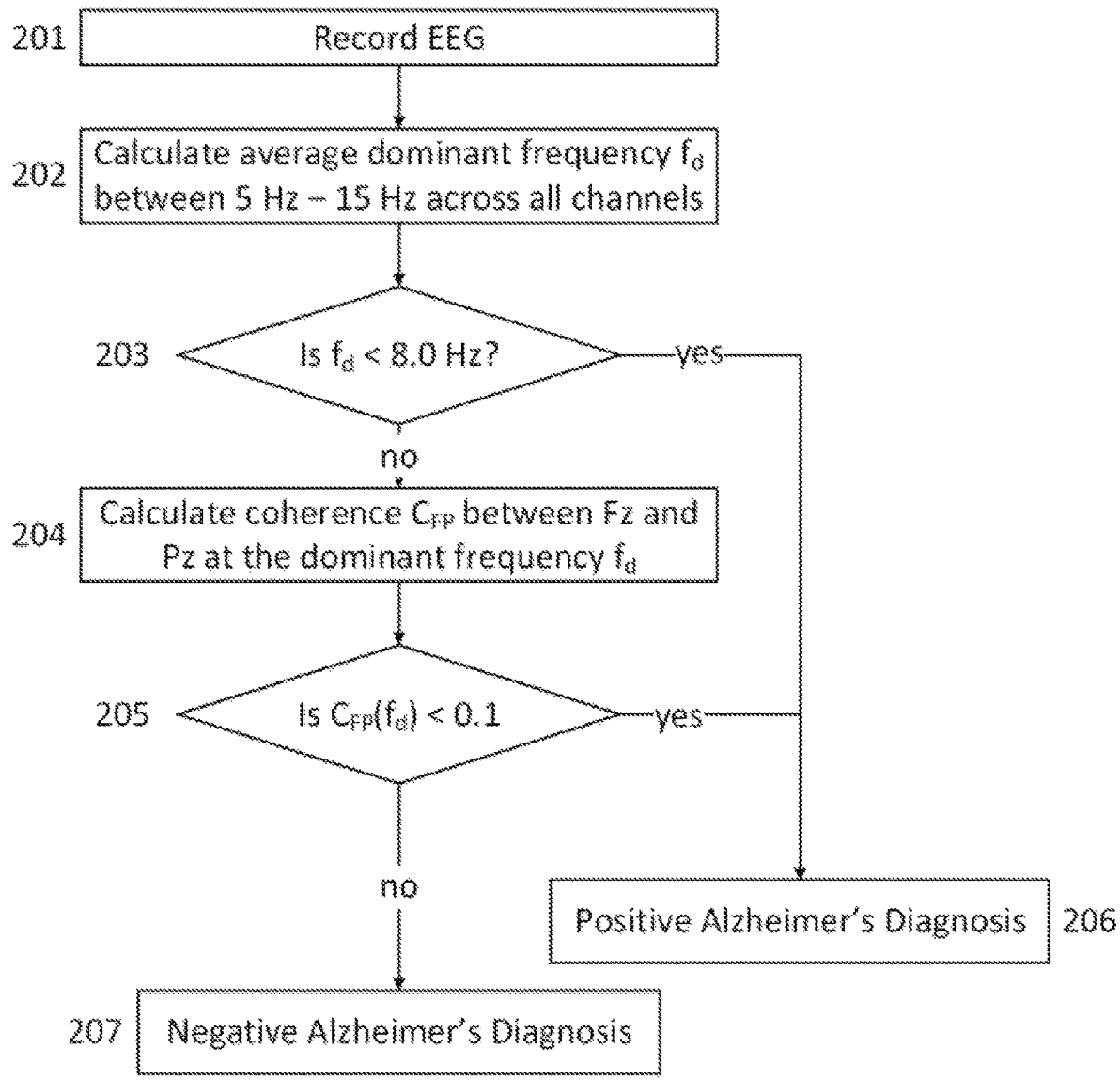
FIG. 2 shows an exemplary system in which a diagnosis of Alzheimer's disease is determined based upon the dominant frequency between 5 Hz-15 Hz, or based upon the EEG coherence between the Fz and Pz locations.

FIG. 2 shows an exemplary flow diagram of the system to diagnose Alzheimer's disease. In this example, the EEG of the person is recorded (201) and the average dominant frequency between about 5 Hz and about 15 Hz across all channels is determined (202). If the dominant frequency is less than 8.0 Hz (203), then a diagnosis of Alzheimer's disease is made (206). Otherwise, the coherence between the Fz EEG channel and the Pz EEG channel is found at the dominant frequency (204), and an Alzheimer's diagnosis is made if the coherence is less than 0.1 (205). If no criteria are met, then an Alzheimer's diagnosis is not appropriate (207).

Figure 3:
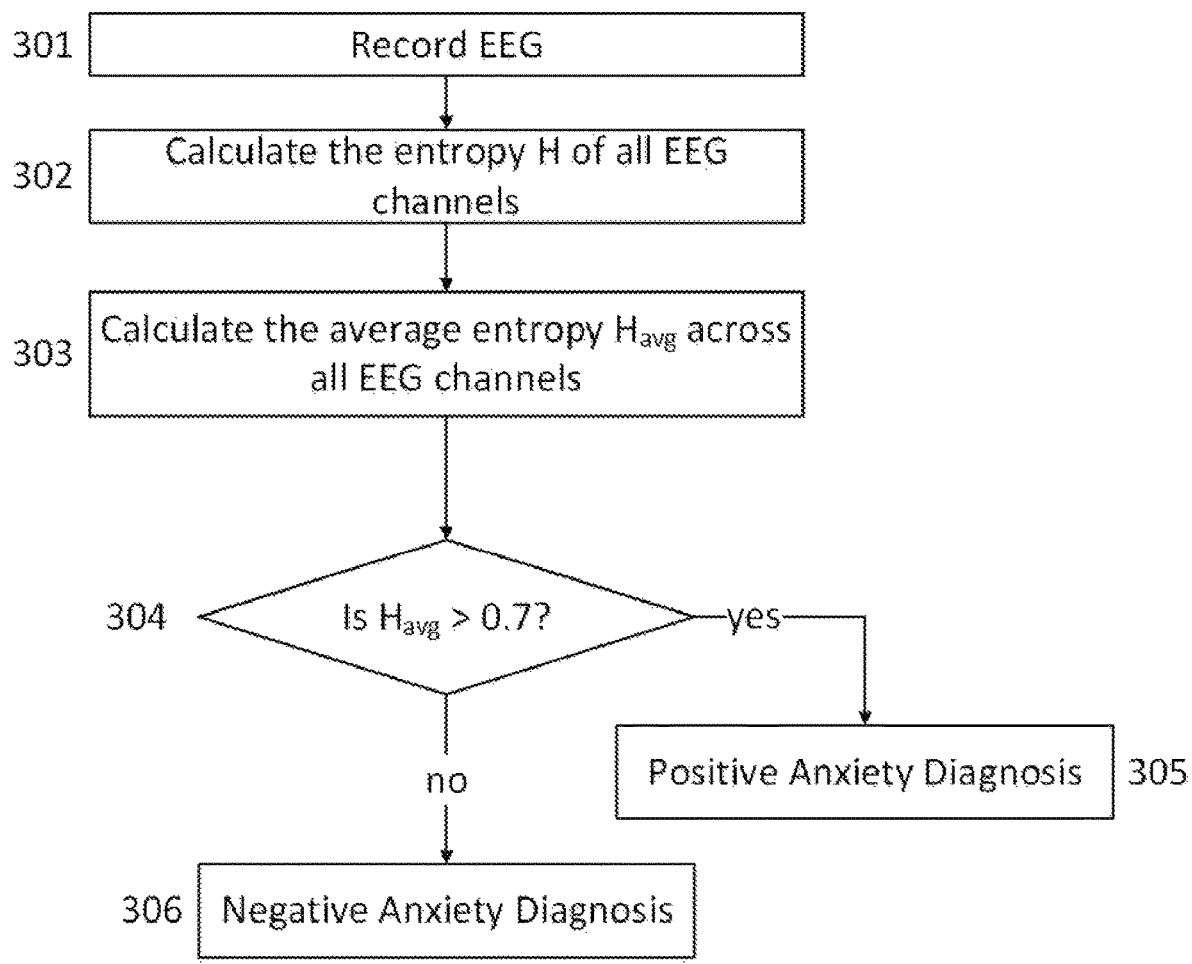
FIG. 3 shows an exemplary system in which a diagnosis of anxiety is determined based upon the average entropy across all EEG channels.

FIG. 3 shows an exemplary flow diagram of the system to diagnose anxiety. In this example, the EEG of the person is recorded (301) and the entropy of each EEG channel is determined (302) and the average of those values is found (303). If this average is greater than 0.7 (304), an anxiety diagnosis is made (305). If not, then an anxiety diagnosis is not appropriate (306).

Figure 4:
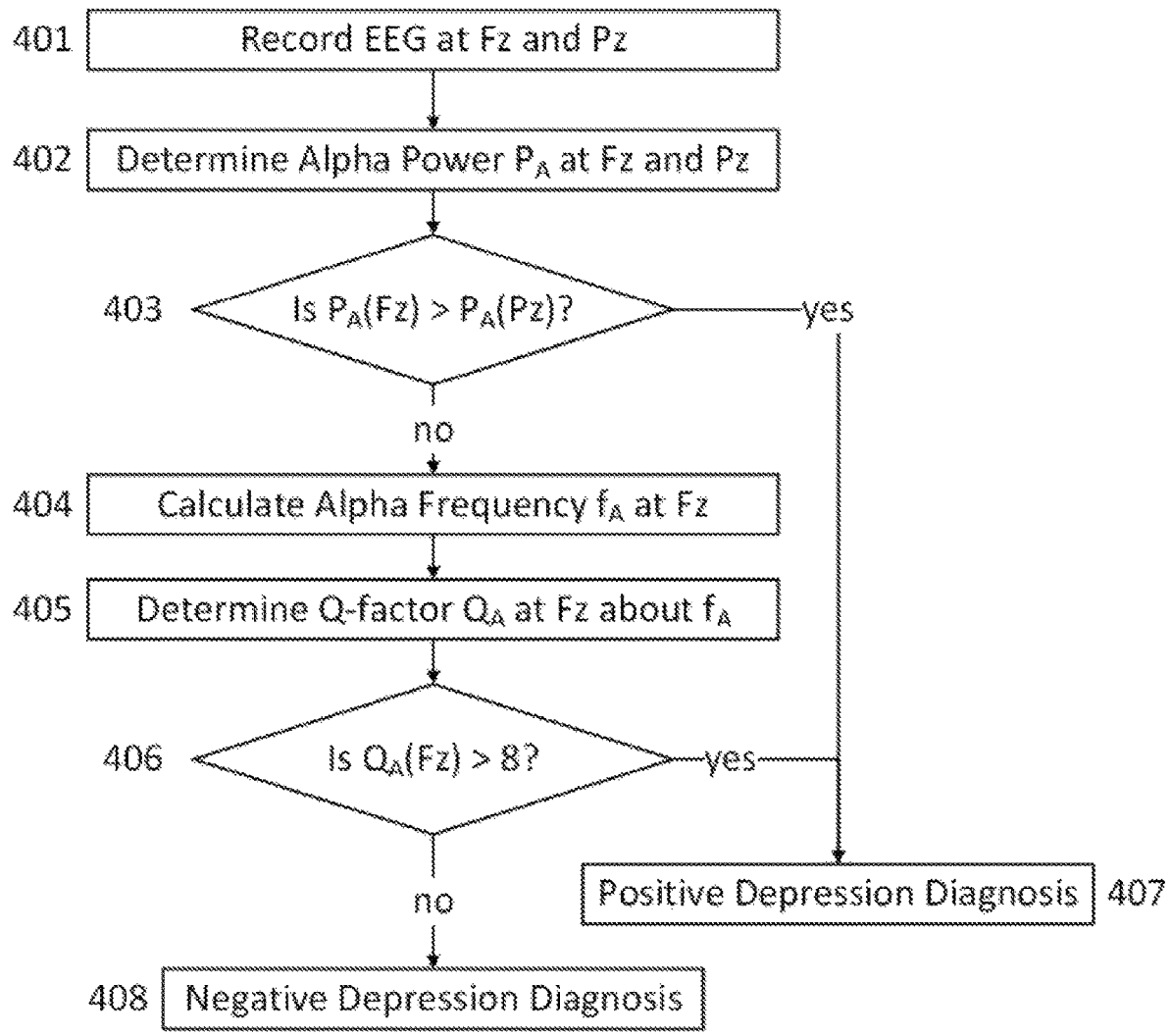
FIG. 4 shows an exemplary system in which a diagnosis of depression is determined based upon the EEG Alpha Power at Fz and Pz, or upon the Q-factor about the EEG alpha frequency at the Fz location.

FIG. 4 shows an exemplary flow diagram of the system to diagnose depression. In this example, the EEG of the person is recorded, specifically at locations Fz and Pz (401). The Alpha Power at Fz and Pz is determined (402), and a depression diagnosis is made (407) if the alpha power at Fz is greater than the alpha power at Pz (403), then a depression diagnosis is made (407). Otherwise, the alpha frequency at Fz is found (404) and the Q-factor is determined at Fz about the alpha frequency (405), and a depression diagnosis is made if the Q-factor is greater than 8 (406). If no criteria are met, a depression diagnosis is not appropriate (408).

Figure 5:
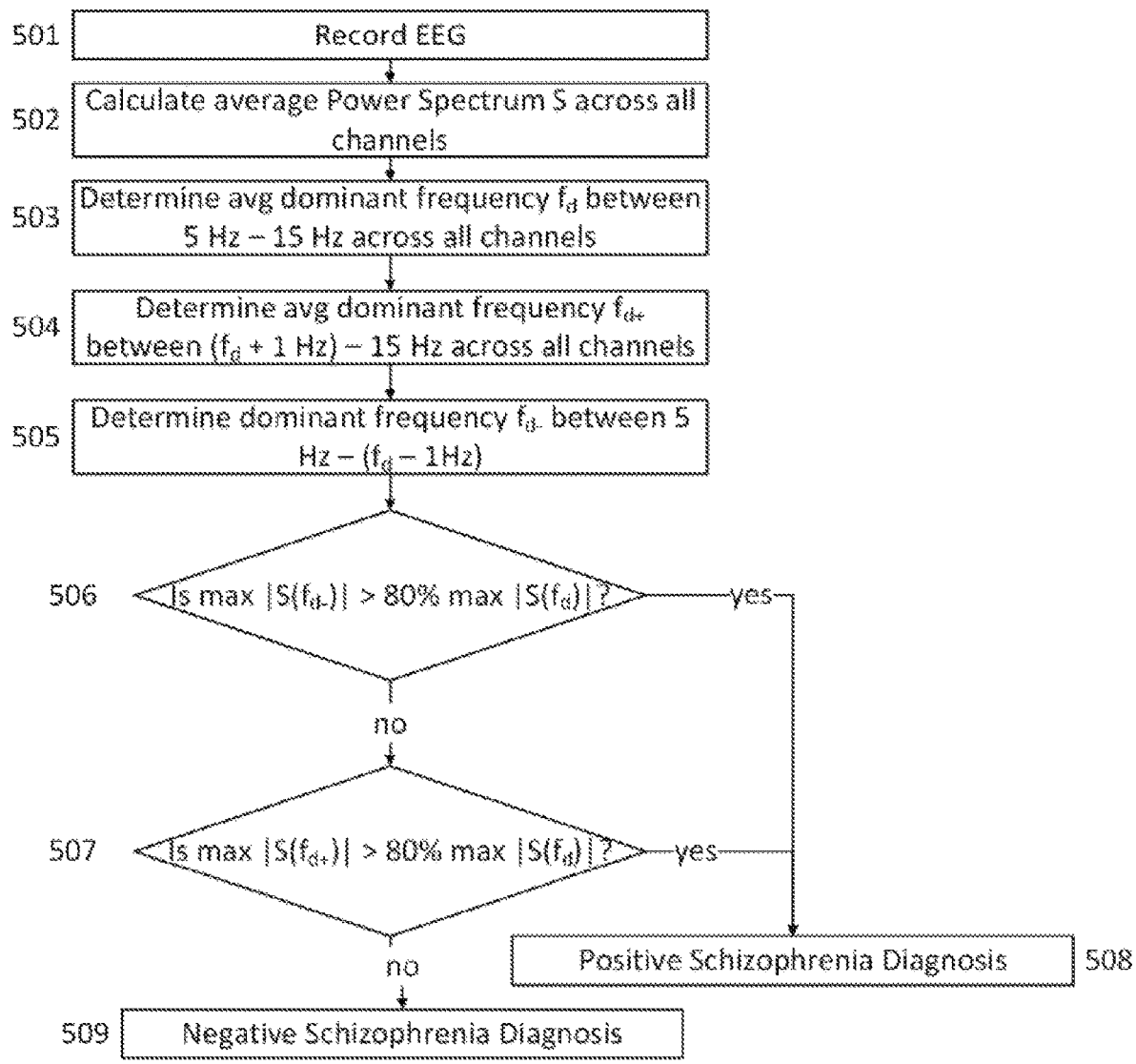
FIG. 5 shows an exemplary system in which a diagnosis of schizophrenia is determined based upon the presence of multiple peaks in the FFT of the EEG channels greater than 1 Hz apart.

FIG. 5 shows an exemplary flow diagram of the system to diagnose schizophrenia. In this example, the EEG of the person is recorded at Fz (501), and the average power spectrum across all channels is found for the EEG at this location (502). The average dominant frequency is determined between 5 Hz-15 Hz across all channels (503). The average upper dominant frequency is found as the average dominant frequency between the dominant frequency +1 Hz and 15 Hz (504). The average lower dominant frequency is found as the average dominant frequency between 5 Hz and the dominant frequency+1 Hz (505). If the magnitude of the power spectrum at the lower dominant frequency is at least 80% the magnitude of the power spectrum at the dominant frequency (506), then a schizophrenia diagnosis is made (508). If the magnitude of the power spectrum at the upper dominant frequency is at least 80% the magnitude of the power spectrum at the dominant frequency (507), then a schizophrenia diagnosis is also made. Otherwise, a schizophrenia diagnosis is not appropriate (509).

Figure 6:
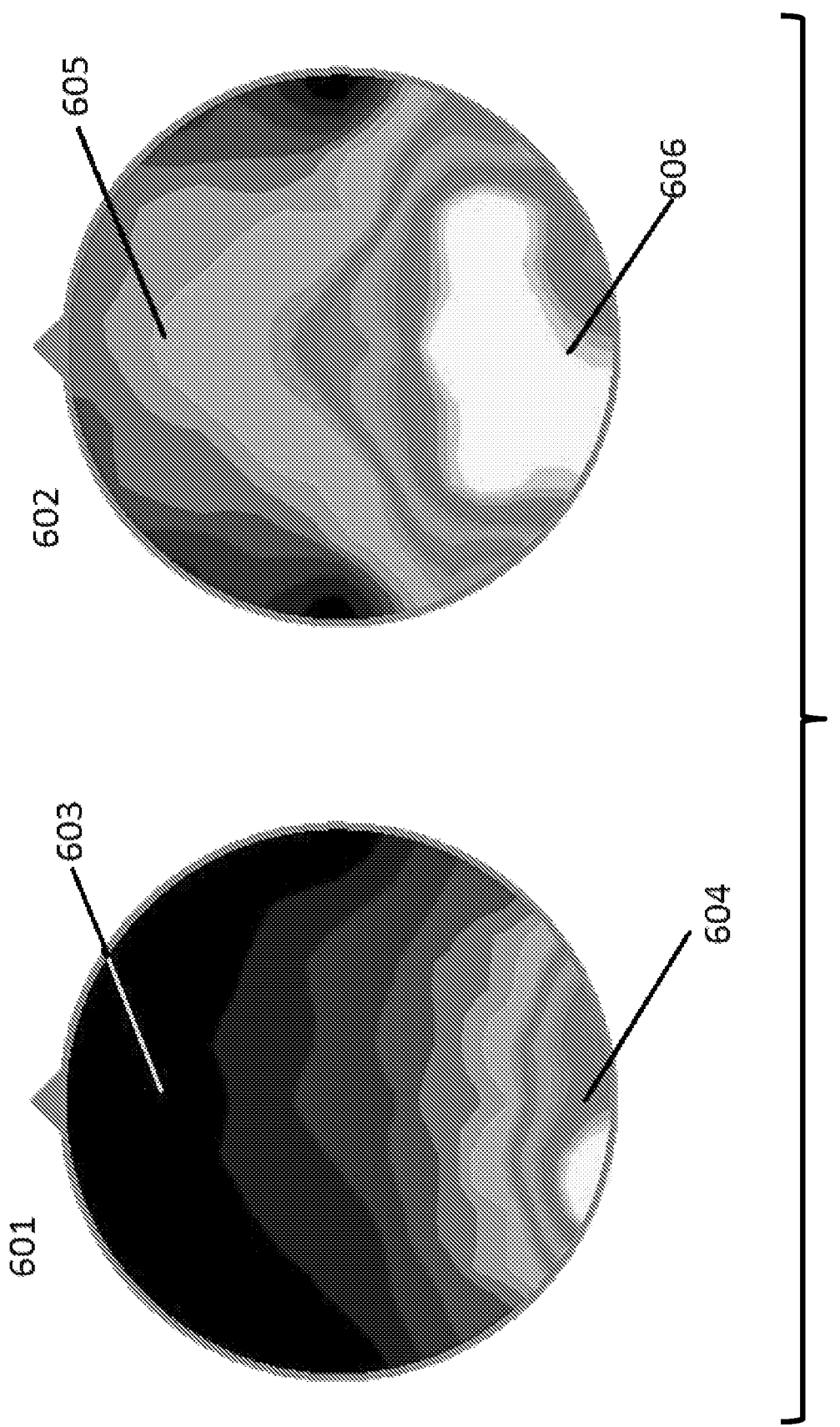
FIG. 6 shows an exemplary 2-D plot of the average relative Alpha Power distribution across all EEG channels for a person with ASD compared to a normal person.

FIG. 6 shows an exemplary 2-D plot of the average relative alpha power distribution across all EEG channels for a person with ASD (601) and a normal person (602). In the plots, the nose is at the top of the plot. The lighter regions in the plot show higher relative alpha power. As can be seen, in the normal person plot, the alpha power in the frontal region (605) is less than in the occipital parietal region (606), though not dramatically so. However, in the ASD person's plot, the alpha power in the frontal region (603) is less than 10% of the alpha power in the occipital-parietal region (604).

Figure 7:
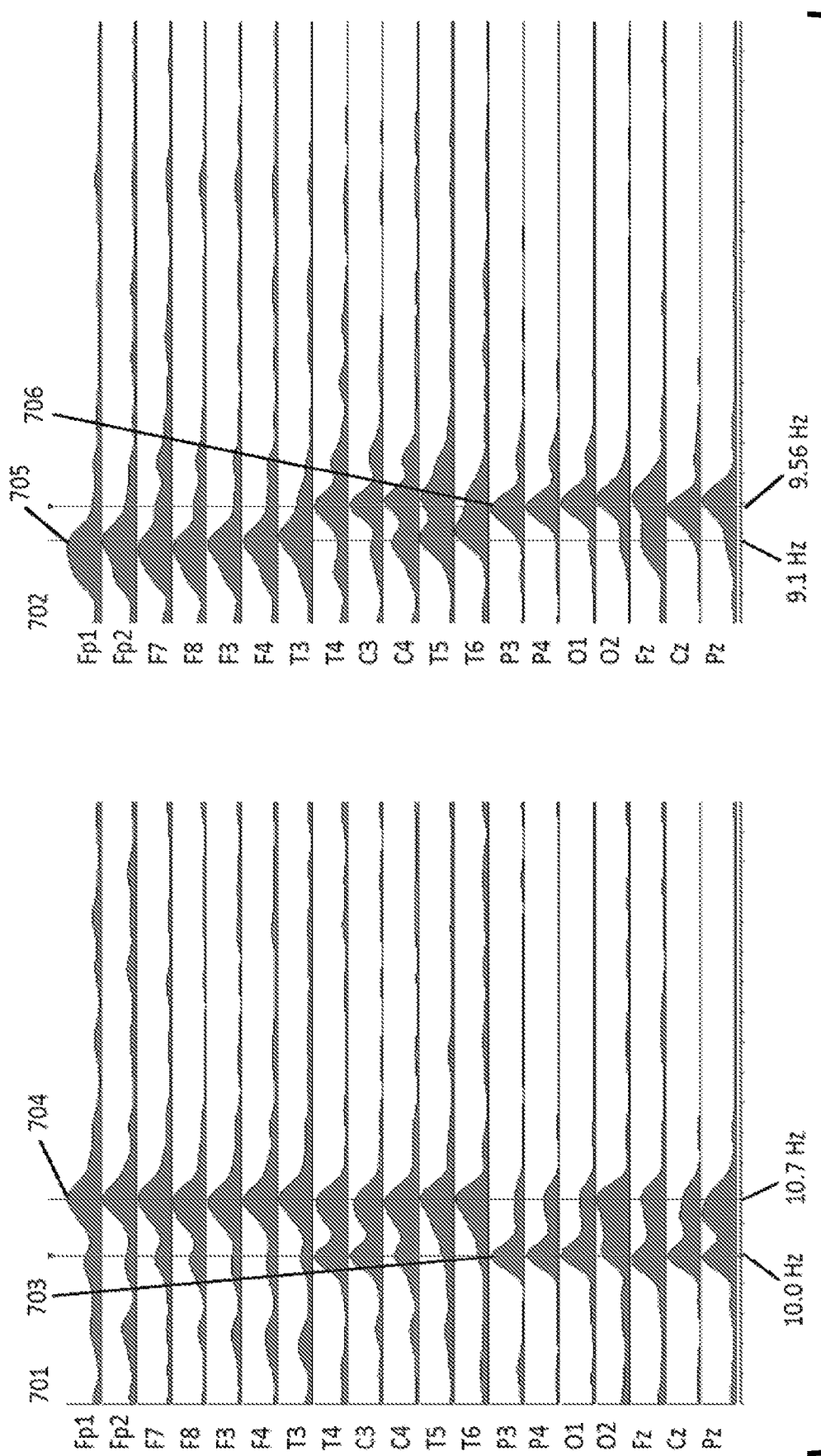
FIG. 7 shows an exemplary graph of the FFT for all EEG channels for a person with ASD compared to a normal person, showing that the dominant peak frequency in the frontal EEG channels for a person with ASD is greater than 0.5 Hz higher than the dominant peak frequency of the occipital-parietal EEG channels, whereas the dominant peak frequency in the frontal EEG channels for a normal person is not higher than the dominant peak frequency of the occipital-parietal EEG channels.

FIG. 7 shows an exemplary graph of the FFT for all EEG channels for a person with ASD (701) compared to a normal person (702). For the person with ASD, it can be seen that the dominant frequency in the occipital parietal region (703) is 10.0 Hz, and the dominant frequency in the frontal region (704) is 10.7 Hz. In this, the alpha frequency in the frontal region is higher than in the occipital-parietal region. For the normal person, however, the reverse is true. The dominant frequency in the frontal region (705) is 9.1 Hz, and the dominant frequency in the occipital-parietal region (706) is 9.56 Hz.

Figure 8:
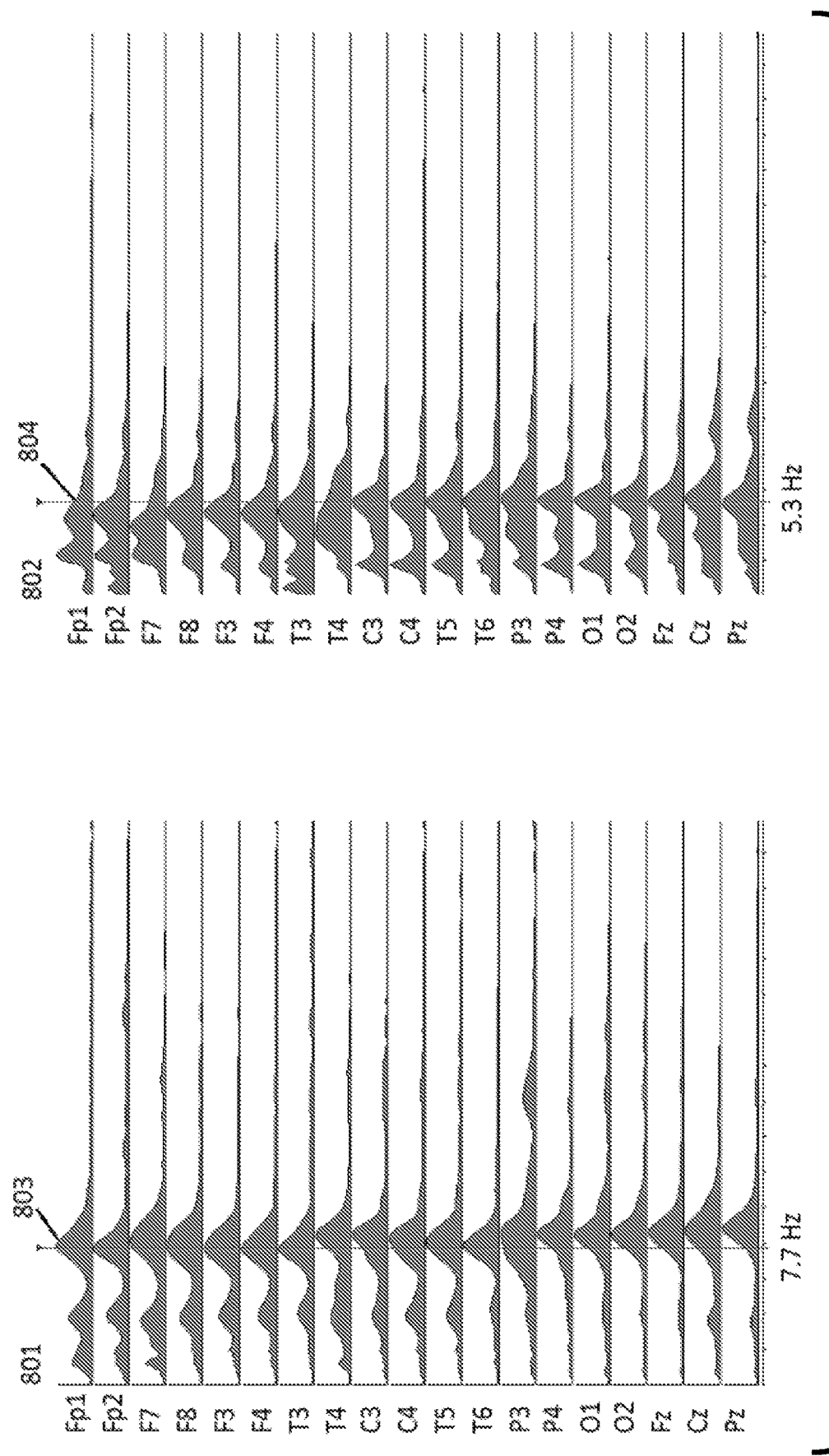
FIG. 8 shows an exemplary graph of the FFT for all EEG channels for a person with mild Alzheimer's disease and a person with severe Alzheimer's disease, showing that the dominant frequency in both cases is less than 8 Hz.

FIG. 8 shows an exemplary graph of the FFT for all EEG channels for a person with mild Alzheimer's disease (801) and a person with severe Alzheimer's disease (802). The alpha frequency for the person with mild Alzheimer's disease (803) is 7.7 Hz. The alpha frequency for the person with severe Alzheimer's disease (804) is 5.3 Hz. Both are less than 8.0 Hz, which would result in an Alzheimer's diagnosis.

Figure 9:
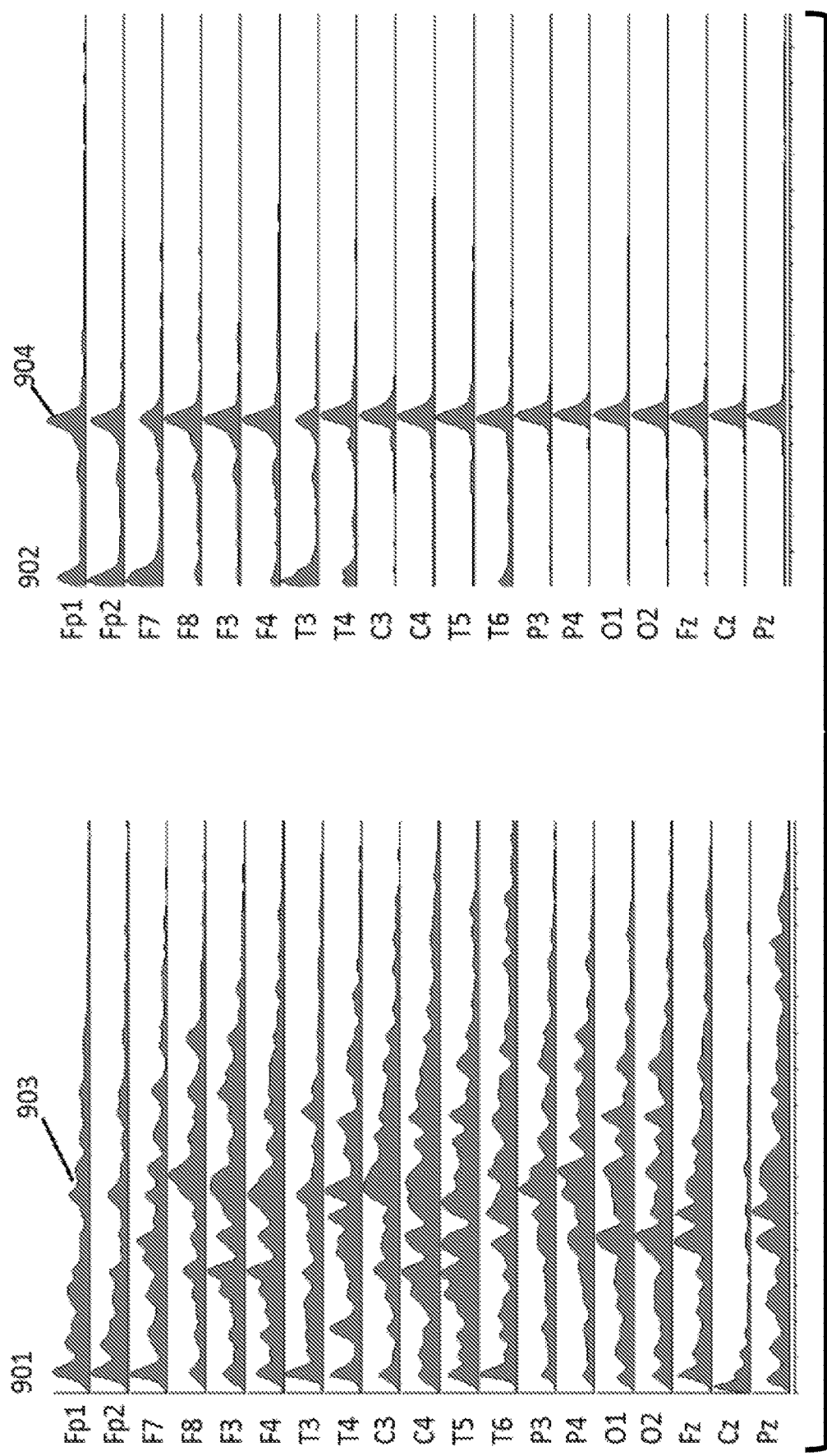
FIG. 9 shows an exemplary graph of the FFT for all EEG channels for a person with anxiety compared to a normal person, showing that the average entropy across all EEG channels is much higher for a person with anxiety.

FIG. 9 shows an exemplary graph of the FFT for all EEG channels for a person with anxiety (901) compared to a normal person (902). In this, the distribution of activity (903) for the person with anxiety covers a much wider spectral range, resulting in a higher entropy value, whereas the distribution of activity (904) for the normal person is much more concentrated about the alpha frequency, and therefore has a lower entropy value.

Figure 10:
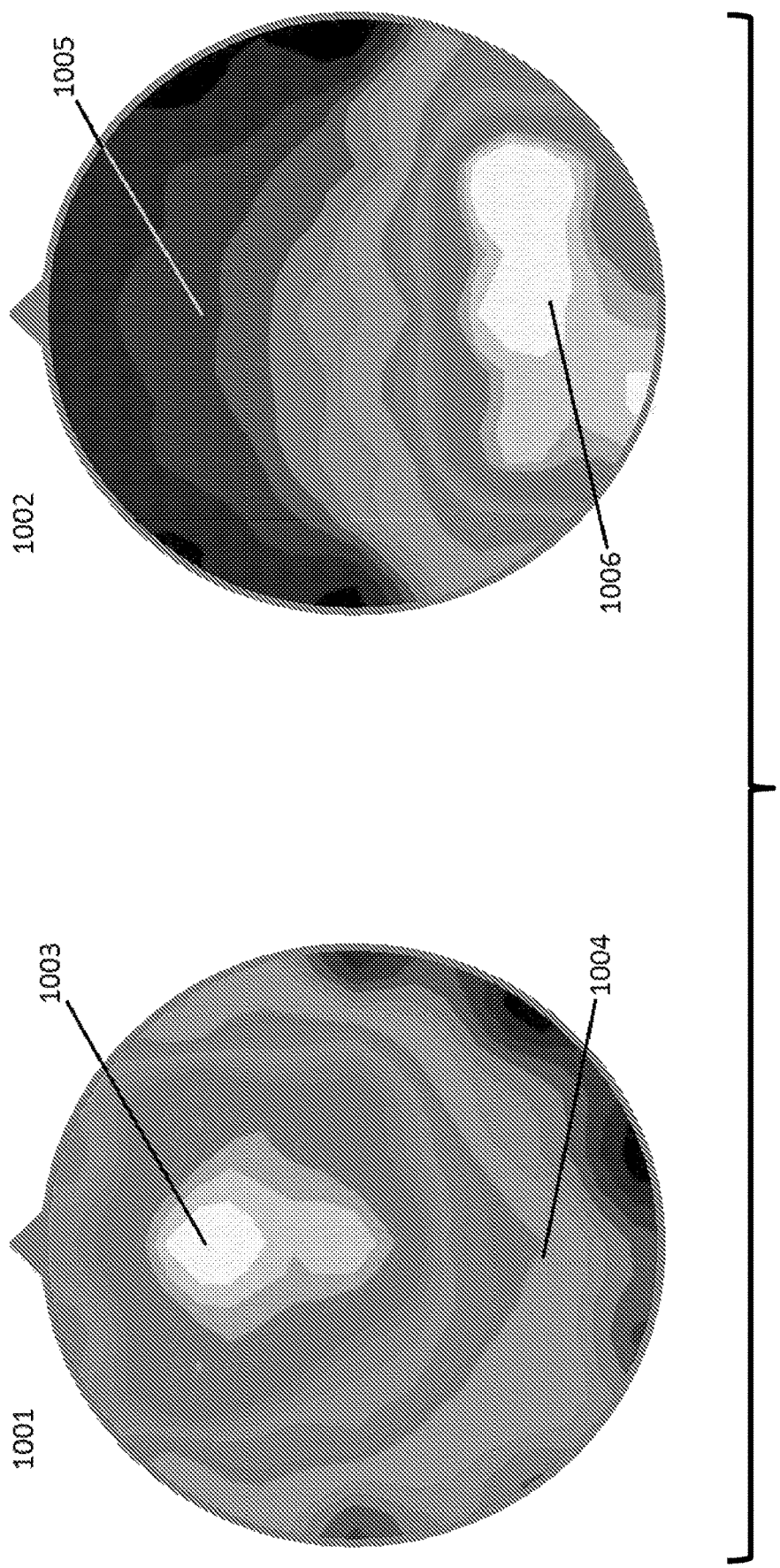
FIG. 10 shows an exemplary 2-D plot of the distribution of Alpha Power across all EEG channels for a person with depression compared to a normal person, showing that the Alpha Power in the frontal EEG channels is higher than the Alpha Power in the occipital-parietal EEG channels for a person with depression.

FIG. 10 shows an exemplary 2-D plot of the distribution of Alpha Power across all EEG channels for a person with depression (1001) compared to a normal person (1002). In the plots, the nose is at the top of the plot. The lighter regions in the plot show higher Alpha Power. For the depressed person, the frontal Alpha Power (1003) is higher than the occipital-parietal Alpha Power (1004), indicating a diagnosis of depression. For the normal person, the frontal Alpha Power (1005) is less than occipital-parietal Alpha Power (1006).

Figure 11:
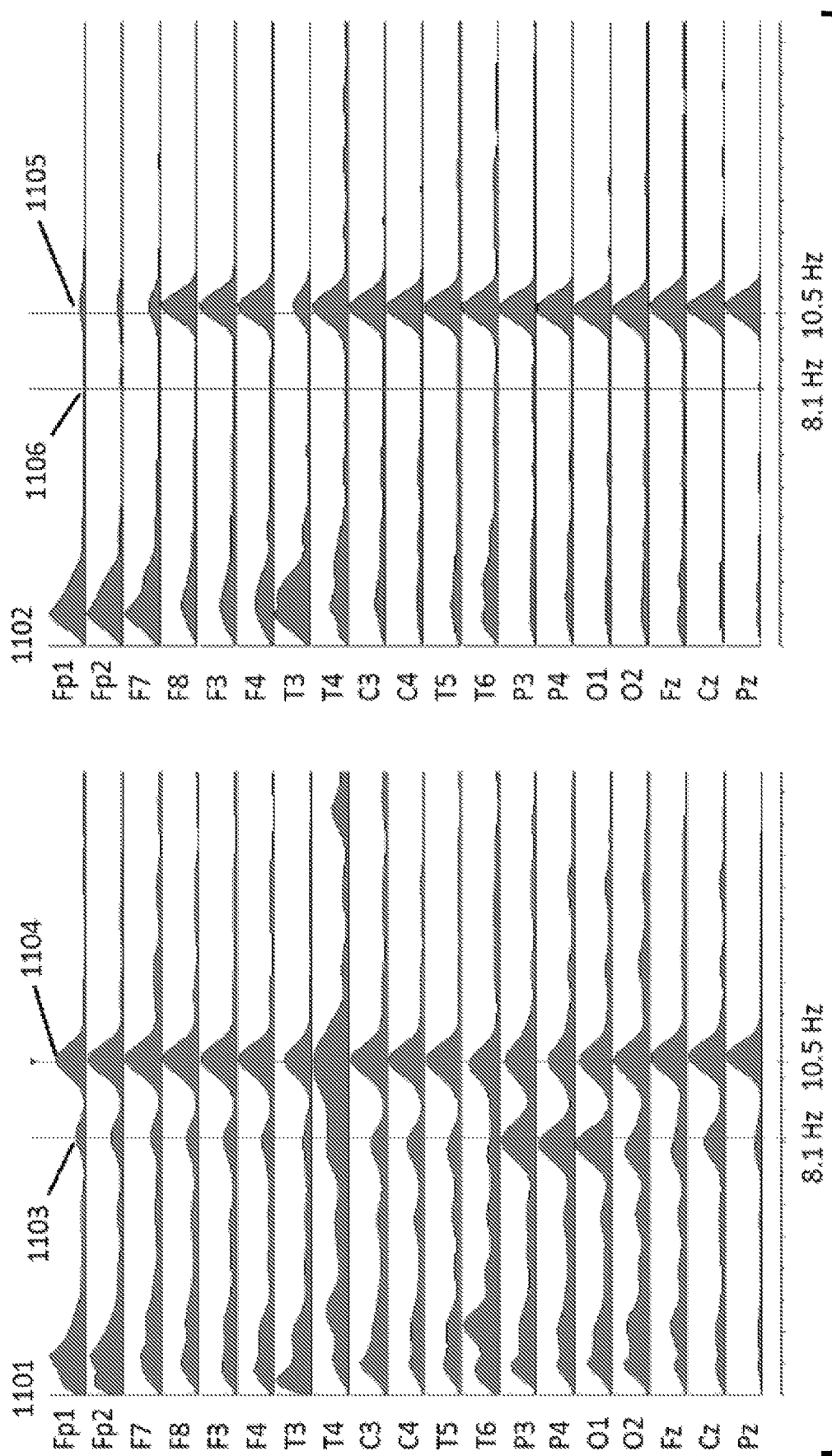
FIG. 11 shows an exemplary graph of the FFT for all EEG channels for a person with schizophrenia compared to a normal person, showing that the FFT for a person with schizophrenia contains two significant dominant peaks more than 1 Hz apart.

FIG. 11 shows an exemplary graph of the FFT for all EEG channels for a person with schizophrenia (1101) compared to a normal person (1102). In this, two dominant peaks exist for the person with schizophrenia, one at 10.5 Hz (1104) and one at 8.1 Hz (1103). For the normal person, only one dominant peak (1105) exists, with no peak in another region in the 5-15 Hz band (1106).

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above descriptions of illustrated embodiments of the system or devices are not intended to be exhaustive or to be limited to the precise form disclosed. While specific embodiments of, and examples for, the system or devices are described herein for illustrative purposes, various equivalent modifications are possible within the scope of the system or devices, as those skilled in the relevant art will recognize. The teachings of the system or devices provided herein can be applied to other processing systems or devices, not only for the systems or devices described.

The elements and acts of the various embodiments described can be combined to provide further embodiments. These and other changes can be made to the system in light of the above detailed description.

In general, in the following claims, the terms used should not be construed to limit the system or devices to the specific embodiments disclosed in the specification and the claims, but should be construed to include all processing systems that operate under the claims. Accordingly, the system and devices are not limited by the disclosure, but instead the scopes of the system or devices are to be determined entirely by the claims.

While certain aspects of the system or devices are presented below in certain claim forms, the inventor contemplates the various aspects of the system or devices in any number of claim forms. Accordingly, the inventors reserve the right to add additional claims after filing the application to pursue such additional claim forms for other aspects of the system or devices.

EXEMPLARY EMBODIMENTS

Specific embodiments of the invention include the following:
1. A system for diagnosing autism spectrum disorder (ASD), wherein the system comprises:
   a. an EEG recording device for recording the EEG of a person;
   b. a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and
   c. a diagnosis mechanism where the system diagnoses the person with ASD if the average relative frontal Alpha Power is less than about 10% of the average relative occipital-parietal Alpha Power.
2. The system of embodiment 1 wherein the diagnosis mechanism is a processor.
3. The system of embodiment 1 wherein the diagnosis mechanism is hand calculation.
4. A system for diagnosing ASD, wherein the system comprises:
   a. an EEG recording device for recording the EEG of a person;
   b. a processing device comprising a processor and internal or external memory, in order to calculate the average relative Alpha Power of EEG signals from at least one of the frontal EEG channels and the average relative Alpha Power of EEG signals from at least one of the occipital-parietal EEG channels; and
   c. a diagnosis mechanism where the system diagnoses the person with ASD if the average relative frontal Alpha Power is less than about 20% of the average relative occipital-parietal Alpha Power and the average relative frontal Alpha Power is less than about 5%.
5. The system of embodiment 4 wherein the diagnosis mechanism is a processor.
6. The system of embodiment 4 wherein the diagnosis mechanism is hand calculation
7. A system for diagnosing ASD, wherein the system comprises:
   a. an EEG recording device for recording the EEG of a person;
   b. a processing device comprising a processor and internal or external memory, in order to calculate the average Alpha Frequency of EEG signals from at least one of the frontal EEG channels and the average Alpha Frequency of EEG signals from at least one of the occipital-parietal EEG channels; and
   c. a diagnosis mechanism where the system diagnoses the person with ASD if the average frontal Alpha Frequency is greater than about 0.5 Hz more than the average occipital-parietal Alpha Frequency.
8. The system of embodiment 7 wherein the diagnosis mechanism is a processor.
9. The system of embodiment 7 wherein the diagnosis mechanism is hand calculation.
10. A system of embodiment 1 or 4 wherein the system diagnoses the person with ASD if the average relative frontal Alpha Power is less than about 10% of the average relative occipital-parietal Alpha Power and the average relative frontal Alpha Power is less than about 5%.
11. A system of embodiment 1 or 7 wherein the system diagnoses the person with ASD if the average relative frontal Alpha Power is less than about 10% of the average relative occipital-parietal Alpha Power and the average frontal Alpha Frequency is greater than about 0.5 Hz more than the average occipital-parietal Alpha Frequency.
12. A system of embodiment 4 or 7 wherein the system diagnoses the person with ASD if the average relative frontal Alpha Power is less than about 20% of the average relative occipital-parietal Alpha Power and the average relative frontal Alpha Power is less than about 5% and the average frontal Alpha Frequency is greater than about 0.5 Hz more than the average occipital-parietal Alpha Frequency.
13. A system for diagnosing Alzheimer's Disease, wherein the system comprises:
   a. an EEG recording device for recording the EEG of a person;
   b. a processing device comprising a processor and internal or external memory, in order to calculate the average dominant frequency between about 5 Hz and 15 Hz of EEG signals from at least one EEG channel; and
   c. a diagnosis mechanism where the system diagnoses the person with Alzheimer's Disease if the average dominant frequency is less than about 8 Hz.
14. The system of embodiment 13 wherein the diagnosis mechanism is a processor.
15. The system of embodiment 13 wherein the diagnosis mechanism is hand calculation.
16. A system for diagnosing Alzheimer's Disease which comprises:
   a. an EEG recording device for recording the EEG of a person;
   b. a processing device comprising a processor and internal or external memory, in order to calculate the average dominant frequency between about 5 Hz and 15 Hz of EEG signals from at least one EEG channel and the average coherence at the dominant frequency between the EEG signals from at least one frontal EEG channel and at least one occipital-parietal EEG channel; and
   c. a diagnosis mechanism where the system diagnoses the person with Alzheimer's Disease if the average coherence is less than about 10%.
17. The system of embodiment 16 wherein the diagnosis mechanism is a processor.
18. The system of embodiment 16 wherein the diagnosis mechanism is hand calculation.
19. A system of embodiment 13 or 16 wherein the system diagnoses the person with Alzheimer's Disease if the dominant frequency is less than about 8 Hz and the average coherence is less than about 10%.
20. A system for diagnosing Anxiety Disorder, wherein the system comprises:
   a. an EEG recording device for recording the EEG of a person;
   b. a processing device comprising a processor and internal or external memory, in order to calculate the average entropy of the EEG signals from at least one EEG channel; and
   c. a diagnosis mechanism where the system diagnoses the person with Anxiety Disorder if the average entropy is greater than about 0.7.
21. The system of embodiment 20 wherein the diagnosis mechanism is a processor.

22. The system of embodiment 20 wherein the diagnosis mechanism is hand calculation.

23. A system for diagnosing Depression, wherein the system comprises:
   a. an EEG recording device for recording the EEG of a person;
   b. a processing device comprising a processor and internal or external memory, in order to calculate the average relative Alpha Power of at least one frontal EEG channel and the average relative Alpha Power of at least one occipital-parietal EEG channel; and
   c. a diagnosis mechanism where the system diagnoses the person with Depression if the average relative frontal Alpha Power is greater than the average relative occipital-parietal Alpha Power.

24. The system of embodiment 23 wherein the diagnosis mechanism is a processor.

25. The system of embodiment 23 wherein the diagnosis mechanism is hand calculation.

26. A system for diagnosing Depression, wherein the system comprises:
   a. an EEG recording device for recording the EEG of a person;
   b. a processing device comprising a processor and internal or external memory, in order to calculate the average frontal Alpha Frequency of EEG signals from at least one frontal EEG channel; and
   c. a diagnosis mechanism where the system diagnoses the person with Depression if the average relative Q factor about the average Alpha Frequency is greater than about 8.

27. The system of embodiment 26 wherein the diagnosis mechanism is a processor.

28. The system of embodiment 26 wherein the diagnosis mechanism is hand calculation.

29. A system of embodiment 23 or 26 wherein the system diagnoses the person with Depression if the average relative frontal Alpha Power is greater than the average relative occipital-parietal Alpha Power and the average relative Q factor is greater than about 8.

30. A system for diagnosing Schizophrenia, wherein the system comprises:
   a. an EEG recording device for recording the EEG of a person;
   b. a processing device comprising a processor and internal or external memory, in order to calculate the average dominant frequency $f_d$ between about 5 Hz and 15 Hz of EEG signals from at least one EEG channel, the average lower dominant frequency between about 5 Hz and about $f_d-1$ Hz of EEG signals from at least one EEG channel, and the average upper dominant frequency between about $f_d+1$ Hz and about 15 Hz of EEG signals from at least one EEG channel; and
   c. a diagnosis mechanism where the system diagnoses the person with Schizophrenia if the magnitude of the average power spectrum from at least one EEG channel at the lower dominant frequency is at least about 80% the magnitude of the average power spectrum from at least one EEG channel at the dominant frequency or the magnitude of the average power spectrum from at least one EEG channel at the upper dominant frequency is at least about 80% the magnitude of the average power spectrum from at least one EEG channel at the dominant frequency.

31. The system of embodiment 30 wherein the diagnosis mechanism is a processor.

32. The system of embodiment 30 wherein the diagnosis mechanism is hand calculation.

While embodiments of the present invention have been shown and described herein, such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that systems and structures within the scope of these claims and their equivalents be covered thereby.

What is claimed is:

1. A system for diagnosing autism spectrum disorder (ASD), comprising:
   an electroencephalogram (EEG) device configured to record an EEG of a person, wherein the EEG device comprises one or more electrodes operable to record
      one or more frontal EEG channels, and
      one or more occipital-parietal EEG channels; and
   a processing device comprising a processor and one or more of internal or external memory, wherein the processing device is configured to
      compute a first average relative Alpha Power of EEG signals based on the one or more frontal EEG channels to output an average relative frontal Alpha Power,
      compute a second average relative Alpha Power of EEG signals based on the one or more occipital-parietal EEG channels to output an average relative occipital-parietal Alpha Power, and
      determine an ASD diagnosis for the person when the average relative frontal Alpha Power is less than 10% of the average relative occipital-parietal Alpha Power.

2. A system for diagnosing autism spectrum disorder (ASD), comprising:
   an electroencephalogram (EEG) configured to record an EEG of a person, wherein the EEG device comprises one or more electrodes operable to record
      one or more frontal EEG channels, and
      one or more occipital-parietal EEG channels; and
   a processing device comprising a processor and one or more of internal or external memory, wherein the processing device is configured to
      compute a first average relative Alpha Power of EEG signals based on the one or more frontal EEG channels to output an average relative frontal Alpha Power,
      compute a second average relative Alpha Power of EEG signals based on the one or more occipital-parietal EEG channels to output an average relative occipital-parietal Alpha Power; and
      determine an ASD diagnosis for the person when the average relative frontal Alpha Power is less than 20% of the average relative occipital-parietal Alpha Power and the average relative frontal Alpha Power is less than 5%.

3. A system for diagnosing autism spectrum disorder (ASD), comprising:
   an electroencephalogram (EEG) device configured to record an EEG of a person, wherein the EEG device comprises one or more electrodes operable to record
      one or more frontal EEG channels, and
      one or more occipital-parietal EEG channels; and a processing device comprising a processor and one or more of internal or external memory, wherein the processing device is configured to
compute a first average Alpha Frequency of EEG signals based on the one or more frontal EEG channels to output an average frontal Alpha Frequency,
compute a second average Alpha Frequency of EEG signals based on the one or more occipital-parietal EEG channels to output an average occipital-parietal Alpha Frequency, and
determine an ASD diagnosis for the person when the average frontal Alpha Frequency is greater than 0.5 Hz more than the average occipital-parietal Alpha Frequency.

4. The system of claim 1 wherein the ASD diagnosis is also determined for the person when the average relative frontal Alpha Power is less than 10% of the average relative occipital-parietal Alpha Power and the average relative frontal Alpha Power is less than 5%.

5. The system of claim 1 wherein the processing device is configured to:
compute a first average Alpha Frequency of EEG signals based on the one or more frontal EEG channels to output an average frontal Alpha Frequency; and
compute a second average Alpha Frequency of EEG signals based on the one or more occipital-parietal EEG channels to output an average occipital-parietal Alpha Frequency,
wherein the ASD diagnosis is determined for the person when the average relative frontal Alpha Power is less than 10% of the average relative occipital-parietal Alpha Power and the average frontal Alpha Frequency is greater than 0.5 Hz more than the average occipital-parietal Alpha Frequency.

6. The system of claim 2 wherein the processing device is configured to:
compute a first average Alpha Frequency of EEG signals based on the one or more frontal EEG channels to output an average frontal Alpha Frequency; and
compute a second average Alpha Frequency of EEG signals based on the one or more occipital-parietal EEG channels to output an average occipital-parietal Alpha Frequency,
wherein the ASD diagnosis is determined for the person when the average relative frontal Alpha Power is less than 20% of the average relative occipital-parietal Alpha Power, the average relative frontal Alpha Power is less than 5%, and the average frontal Alpha Frequency is greater than 0.5 Hz more than the average occipital-parietal Alpha Frequency.

7. The system of claim 2 wherein the ASD diagnosis is determined for the person when the average relative frontal Alpha Power is less than 10% of the average relative occipital-parietal Alpha Power and the average relative frontal Alpha Power is less than 5%.

8. The system of claim 3 wherein the processing device is configured to:
compute a first average relative Alpha Power of EEG signals based on the one or more frontal EEG channels to output an average relative frontal Alpha Power; and
compute a second average relative Alpha Power of EEG signals based on the one or more occipital-parietal EEG channels to output an average relative occipital-parietal Alpha Power,
wherein the ASD diagnosis is determined for the person when the average relative frontal Alpha Power is less than 10% of the average relative occipital-parietal Alpha Power and the average frontal Alpha Frequency is greater than 0.5 Hz more than the average occipital-parietal Alpha Frequency.

9. The system of claim 3 wherein the processing device is configured to:
compute a first average relative Alpha Power of EEG signals based on the one or more frontal EEG channels to output an average relative frontal Alpha Power; and
compute a second average relative Alpha Power of EEG signals based on the one or more occipital-parietal EEG channels to output an average relative occipital-parietal Alpha Power,
wherein the ASD diagnosis is determined for the person when the average relative frontal Alpha Power is less than 20% of the average relative occipital-parietal Alpha Power, the average relative frontal Alpha Power is less than 5%, and the average frontal Alpha Frequency is greater than 0.5 Hz more than the average occipital-parietal Alpha Frequency.

* * * * *